United States Patent
Szinicz (10) Patent No.: US 8,394,012 B2
(45) Date of Patent: *Mar. 12, 2013

(54) DEVICE FOR USE FOR THE TREATMENT OF HEMORRHOID PROLAPSE

(75) Inventor: Gerhard Szinicz, Bregenz (AT)

(73) Assignee: A.M.I. Agency for Medical Innovations GmbH (AU)

( * ) Notice: Subject to any disclaimer, the term of this patent is extended or adjusted under 35 U.S.C. 154(b) by 153 days.

This patent is subject to a terminal disclaimer.

(21) Appl. No.: 12/597,400

(22) PCT Filed: Apr. 4, 2008

(86) PCT No.: PCT/AT2008/000123
§ 371 (c)(1),
(2), (4) Date: Oct. 23, 2009

(87) PCT Pub. No.: WO2008/128261
PCT Pub. Date: Oct. 30, 2008

(65) Prior Publication Data
US 2010/0130857 A1    May 27, 2010

(30) Foreign Application Priority Data
Apr. 23, 2007   (AT) ................... A 632/2007

(51) Int. Cl.
*A61B 1/00*    (2006.01)

(52) U.S. Cl. ........ 600/106; 600/437; 600/446; 600/221; 600/104; 600/114; 600/136; 600/137; 600/184

(58) Field of Classification Search .................. 600/104, 600/105, 114, 135–138, 184, 197–198, 221, 600/29, 37, 454, 446, 437
See application file for complete search history.

(56) References Cited

U.S. PATENT DOCUMENTS
(Continued)

FOREIGN PATENT DOCUMENTS
AT    501766 A1    11/2006
DE    8316987.3 U1   11/1983
(Continued)

OTHER PUBLICATIONS

Search Report of the Austrian priority application A 632/2007 of Apr. 23, 2007 together with a translation of its essential parts.
(Continued)

*Primary Examiner* — Brian Casler
*Assistant Examiner* — Amanda Lauritzen
(74) *Attorney, Agent, or Firm* — Brooks Kushman P.C.

(57) ABSTRACT

A device for use for the treatment of a hemorrhoid prolapse, particularly by HAL surgery, attaching a tightening suture, or a rubber band ligation, using a tube having a tube shell wall and a closing device having a closure shell wall enclosing a hollow space. The tube shell wall is supported displaceably and/or rotatably in the hollow space of the closure shell wall, and the tube shell wall and the closure shell wall can be inserted into a rectum of a patient. The tube shell wall has at least one tube wall opening, and the closure shell wall has at least one closure shell opening which can be at least partially aligned with one another in an open position with a web arranged thereof protruding at least partially into the tube shell opening and/or into the closure shell opening.

23 Claims, 4 Drawing Sheets

U.S. PATENT DOCUMENTS

| | | | |
|---|---|---|---|
| 295,798 A | 3/1884 | Pagett | |
| 5,025,778 A | 6/1991 | Silverstein et al. | |
| 5,570,692 A | 11/1996 | Morinaga | |
| 6,126,594 A | 10/2000 | Bayer | |
| 6,142,931 A | 11/2000 | Kaji | |
| 6,142,933 A | 11/2000 | Longo et al. | |
| 6,632,227 B2 | 10/2003 | Adams | |
| 7,235,043 B2 * | 6/2007 | Gellman et al. | 600/29 |
| 7,695,432 B2 * | 4/2010 | Scheyer | 600/184 |
| 2003/0130559 A1 | 7/2003 | Morin et al. | |
| 2004/0267088 A1 * | 12/2004 | Kammerer | 600/37 |
| 2005/0234305 A1 * | 10/2005 | Licciardi | 600/221 |
| 2006/0009797 A1 | 1/2006 | Armstrong | |
| 2006/0036129 A1 | 2/2006 | Sias | |
| 2006/0167473 A1 | 7/2006 | Scheyer | |
| 2008/0281204 A1 * | 11/2008 | Salfi et al. | 600/454 |

FOREIGN PATENT DOCUMENTS

| | | |
|---|---|---|
| DE | 10231004 A1 | 1/2004 |
| EP | 1234539 A2 | 8/2002 |
| EP | 1683473 A1 | 7/2006 |
| WO | 9221279 A1 | 12/1992 |
| WO | 2004064624 A1 | 8/2004 |
| WO | 2007016946 A1 | 2/2007 |

OTHER PUBLICATIONS

Search Report of the Austrian patent application A 108/2005 of Jan. 25, 2005 together with a translation of its essential parts.
Search Report of the Austrian patent application A 1438/2005 of Sep. 2, 2005 together with a translation of its essential parts.
Search Report of the European patent application 06 000 772.1 of Jan. 14, 2006 together with a translation of its essential parts.

* cited by examiner

DEVICE FOR USE FOR THE TREATMENT OF HEMORRHOID PROLAPSE

The present invention relates to a device for use in the treatment of a hemorrhoid prolapse, particularly by a HAL operation and/or application of a purse-string suture and/or a rubber band ligature, having a tube with a tube shell wall and a closing device with a closure shell wall enclosing a hollow space, wherein the tube shell wall can be mounted displaceably and/or rotatably in the hollow space of the closure shell wall, and the tube shell wall and the closure shell wall can be inserted, individually or jointly, into a rectum of a patient, wherein the tube shell wall has at least one tube shell opening, and the closure shell wall has at least one closure shell opening, and the tube shell opening and the closure shell opening can be made to lie at least partially congruent with each other in at least one open position.

It is already known to perform a minimally invasive hemorrhoid artery ligation by means of an ultrasound probe to be inserted into the rectum. An ultrasound sensor is arranged in the distal area of a tube, specifically next to an opening in the shell wall of the tube. A hemorrhoid artery in the intestinal wall is located by means of the ultrasound sensor, after which the artery is ligated or a HAL operation performed through the opening in the tube. In addition to its minimally invasive nature, an advantage of this now commonly used treatment method is that the treatment takes place in the area of the intestinal wall above the pectinate line and therefore not in an area that is sensitive to pain. However, in the case of a grade III or IV hemorrhoid prolapse, this method may not provide the successful outcome desired. These grades involve extensive prolapsed hemorrhoid nodules or prolapsed mucosa, which prolapse to a more or less pronounced extent and more or less permanently from the anus. Such devices for hemorrhoid artery ligation are known, for example, from U.S. Pat. No. 5,570,692 A and EP 1 234 539 A2. The latter document also shows a rubber band ligation in FIG. 12.

Moreover, various operations have already been carried out in which the prolapsed nodules are tightened by means of purse-string sutures in order to substantially reduce the prolapse. However, these operations have proven technically difficult since, depending on the findings, the prolapse of the mucous membrane makes accurate punctures in this area difficult, maintaining a sufficient distance from the pectinate line is difficult to control (resulting in pain), and the time needed for the individual punctures is too great (four to five punctures are in most cases needed to achieve a successful outcome).

A device of this kind for improving this operating technique is already known from EP 1 683 473 A1. In the device proposed there, an operation gap, through which the mucosa can be reached, can be successively enlarged by successively rotating the closing device relative to the tube, starting from the distal end of the device. The operation gap is obtained by means of the tube shell opening being brought into a position at least partially congruent with the closure shell opening. However, it has been found in practice that the effective opening of the operation gap, increasing in size between tube shell opening and closure shell opening, becomes too large, with the result that the mucosa penetrates too far into the interior of the tube.

A device whose basic structure is similar to the one in EP 1 683 473 A1 is disclosed in U.S. Pat. No. 295,798. There, the tube shell opening is enlarged in stages. There is therefore once again a possibility of the mucosa penetrating too far into the interior of the tube.

The object of the invention is to improve a device of the type in question in such a way that the mucosa is prevented from penetrating too far into the interior of the tube.

This is achieved by a device having the features of patent claim 1.

The bar or bars still ensure, on the one hand, the possibility of reaching, with corresponding surgical instruments known per se, from the interior of the tube through the tube shell opening and the closure shell opening to the mucosa that is to be operated on. However, on the other hand, the bar or bars also support the mucosa in such a way that the mucosa is prevented from penetrating too deeply into the interior of the tube. The bar or bars thus divide the operation opening or operation window into individual openings which are preferably arranged one behind the other in the longitudinal direction of the tube and through which surgery can be performed.

Provision is preferably made that, before the operation, the device can be inserted into the rectum of the patient in a closed position in which both the closure shell opening and also the tube shell opening are closed. Shortly before the operation, and preferably by turning the closing device relative to the tube, an operation window is opened by means of the tube shell opening and closure shell opening being made congruent. In this so-called open position, the bars according to the invention remain in the operation window, as a result of which the mucosa is supported during the operation. To permit the turning of the closing device relative to the tube, provision is expediently made that, apart from openings provided therein, the tube shell wall and/or the closure shell wall are/is at least partially rotationally symmetrical with respect to a longitudinal axis and are preferably cylindrical or conical or frustoconical.

The invention thus makes available a device which permits very versatile use and with which it is possible to perform a known HAL or ligation operation and also to apply a purse-string suture or also a rubber band ligature. Particularly for creating a purse-string suture, it is expedient that the tube shell opening and/or the closure shell opening are/is elongate between their distal end and their proximal end.

For optimal support of the mucosa during the operation, it is expedient if each web is spaced apart from the distal end and from the proximal end of the tube shell opening and/or of the closure shell opening.

In the case of several bars, it is preferable that each two adjacent bars are spaced apart from each other and/or extend parallel to each other, preferably in the longitudinal direction of the tube shell wall and/or the closure shell wall.

Various types of shape and arrangement of the bars are possible in principle. However, it is preferable if each web or bar is elongate and its longitudinal extent is substantially perpendicular to a longitudinal axis of the tube shell wall and/or of the closure shell wall. Substantially perpendicular is preferably to be understood as meaning an angle of between 70.degree. and 110.degree., very preferably of between 80.degree. and 100.degree. A longitudinal extent is to be generally understood as meaning that the extent of an object in the longitudinal direction is substantially greater than the extent in the transverse direction, that is to say preferably at least twice the extent in a transverse direction.

With reference to the device according to the invention, the terms distal and proximal are to be understood in relation to the end directed toward the operator. Thus, the distal end of the device is the insertion end of the tube, and the proximal end is the opposite end of the device.

Further embodiments and features of the invention are explained on the basis of a preferred illustrative embodiment of the invention shown in the figures, where:

FIGS. 6a to 7 show a specific type of use of the tube of the device for a rubber band ligation.

Figures 1A, 1B, 2:
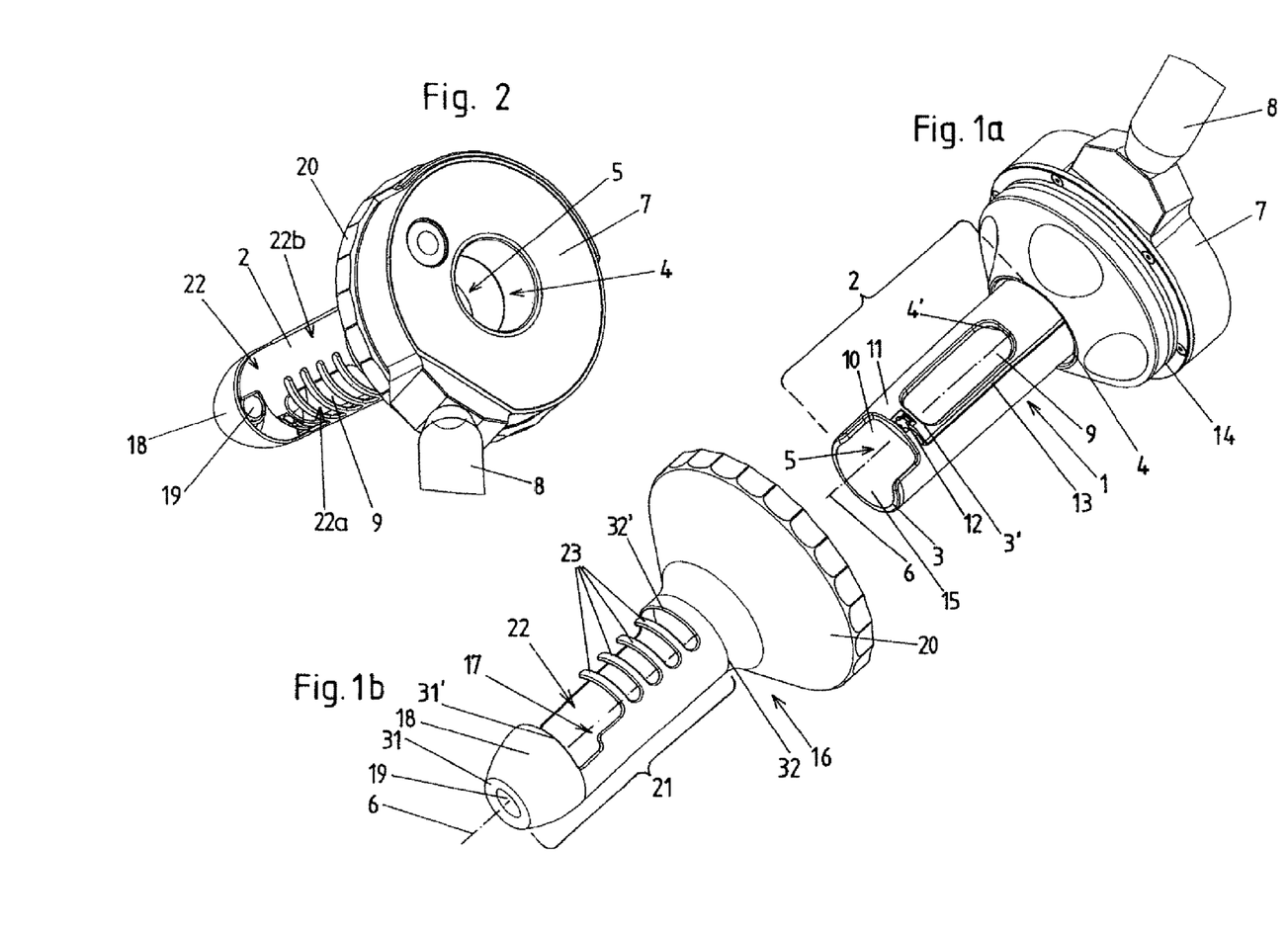
FIGS. 1a and 1b show an exploded view of the tube and of the closing device of the illustrative embodiment.
FIG. 2 shows a view of the proximal end of the device.

FIG. 1a first shows a tube 1 secured on the holder 7. The holder 7, as is known per se, carries a handgrip 8. The tube 1 has, apart from the tube shell opening 9 and the ligature opening 10, a tube shell wall 2 that is rotationally symmetrical with respect to the longitudinal axis 6. The tube shell wall 2 extends from its distal end 3 to its proximal end 4. An ultrasound sensor 12 known per se is arranged on an intermediate web 11 of the tube shell wall 2 between the tube shell opening 9, which likewise extends in the direction of the longitudinal axis 6, and the ligature opening 5, which is arranged distally from the tube shell opening 9. The supply lines for the ultrasound sensor 12 are concealed in the channel 13. The ultrasound sensor 12 serves to locate an artery. Depending on the orientation of the ultrasound sensor 12, it can locate this artery in the area of the ligature opening 10 or of the tube shell opening 9.

As is shown further below with reference to FIGS. 4a and 5a, the ligature opening 10 in this preferred illustrative embodiment is used for performing a HAL operation, while the purse-string suture can be applied to the mucosa through the tube shell opening 9 that extends in elongate form between its distal end 3' and its proximal end 4'. However, it does not necessarily have to be so. It is entirely conceivable to dispense with the ligature opening 10 and to perform the HAL operation in the distal end area of the tube shell opening 9. In this embodiment, the tube shell opening 9 can be made suitably long, and the ultrasound sensor 12 can locate the artery in the area of the tube shell opening 9.

FIG. 1b shows the closing device 16 in this illustrative embodiment, into the hollow space 17 of which the tube shell wall 2 can be inserted. Provision is preferably made here that the shape of the outer surface of the tube shell wall 2 corresponds so exactly to the shape of the inner surface of the closure shell wall 21 that, upon insertion of the tube shell wall 2 into the hollow space 17 of the closure shell wall 21, a snug fit can be obtained, except for the play required for insertion and turning.

For exact guidance, the closing device 16 has a guide portion 20 which, in the assembly position according to FIGS. 2 to 5, engages with the guide 14 of the holder 17 of the tube 1. At least in its central area and proximal area, the closure shell wall 21 receiving the tube shell wall 2 is rotationally symmetrical with respect to the longitudinal axis 6, apart from the closure shell opening 22 and also the tube shell wall 2, and is substantially cylindrical. Its distal end is designated by 31 and its proximal end by 32. The distal portion 18 is conically rounded to facilitate insertion into the rectum of the patient. In this illustrative embodiment, the tube shell wall 2 and the closure shell wall 21 have a distal open end. By way of the corresponding openings 15 and 19, it is possible for the surgeon to guide an instrument through the open distal end of the device during surgery in order to use this instrument to press prolapsed mucous membrane in the distal direction, e.g. to support tightening and to relieve the load on the suture that is to be applied. A closed configuration of the distal end of the tube 1 and/or of the closing device 16 is conceivable and possible, but less preferable.

The closure shell opening 22 is of such a size that, at a suitable angled position between the closing device 16 and the tube 1 inserted into the hollow space 17 of the closing device 16, it frees both the tube shell opening 9 and also the ligature opening 5, in other words is congruent with these. The closure shell opening 22 extends in the longitudinal direction between the distal end 31' and the proximal end 32'. According to the invention, the bars 23 are provided to support the mucosa during the operation. In this illustrative embodiment, they are formed integrally on the closure shell wall 21. In addition, the bars 23 are curved in the circumferential direction 33 according to the closure shell wall 21. The web-s bars 23 in this illustrative embodiment, which are spaced apart from and parallel to one another, extend over only a first portion 22a of the closure shell opening 22. A second portion 22b of the closure shell opening 22 remains entirely free of bars 23 along the entire length of the closure shell opening 22 between distal end 31' and proximal end 32'. These bars 23 thus each have one end free and one end arranged on or integrally formed on the closure shell wall 21. In this way, a generally comb-like or rake-like structure is obtained by means of the bars 23. The number of bars 23 can vary depending on the desired distance and density of the stitches to be made in the mucosa. It is expedient to provide between two and six, preferably between three and five bars 23. In the illustrative embodiment shown, the bars 23 are arranged exclusively on the closure shell wall 21. This does not have to be the case, however. It is entirely possible for corresponding bars 23 to be arranged on the tube shell wall 2 or in the tube shell opening 9. It is even conceivable to arrange webs 23 on tube shell wall 2 and closure shell wall 21, which can produce a structure with two overlapping combs. In addition, it is also possible in some cases, when using a suitable operating technique, to dispense with the free ends of the bars 23 and with the portion 22b. In this case, the bars 23 then extend across the whole closure shell opening 22 and/or tube shell opening 9.

FIG. 2 shows the proximal end of the device. The hollow space 5 open toward the proximal end 4 of the tube 1 can be seen. As is known per se, surgical instruments, lighting devices, suction devices and the like can be inserted into the inner hollow space 5 of the tube. A number of surgical instruments and suitable forms of lighting are described and disclosed, for example, in EP 1 683 473 and in EP 1 234 539.

Figures 3, 4, 4A:
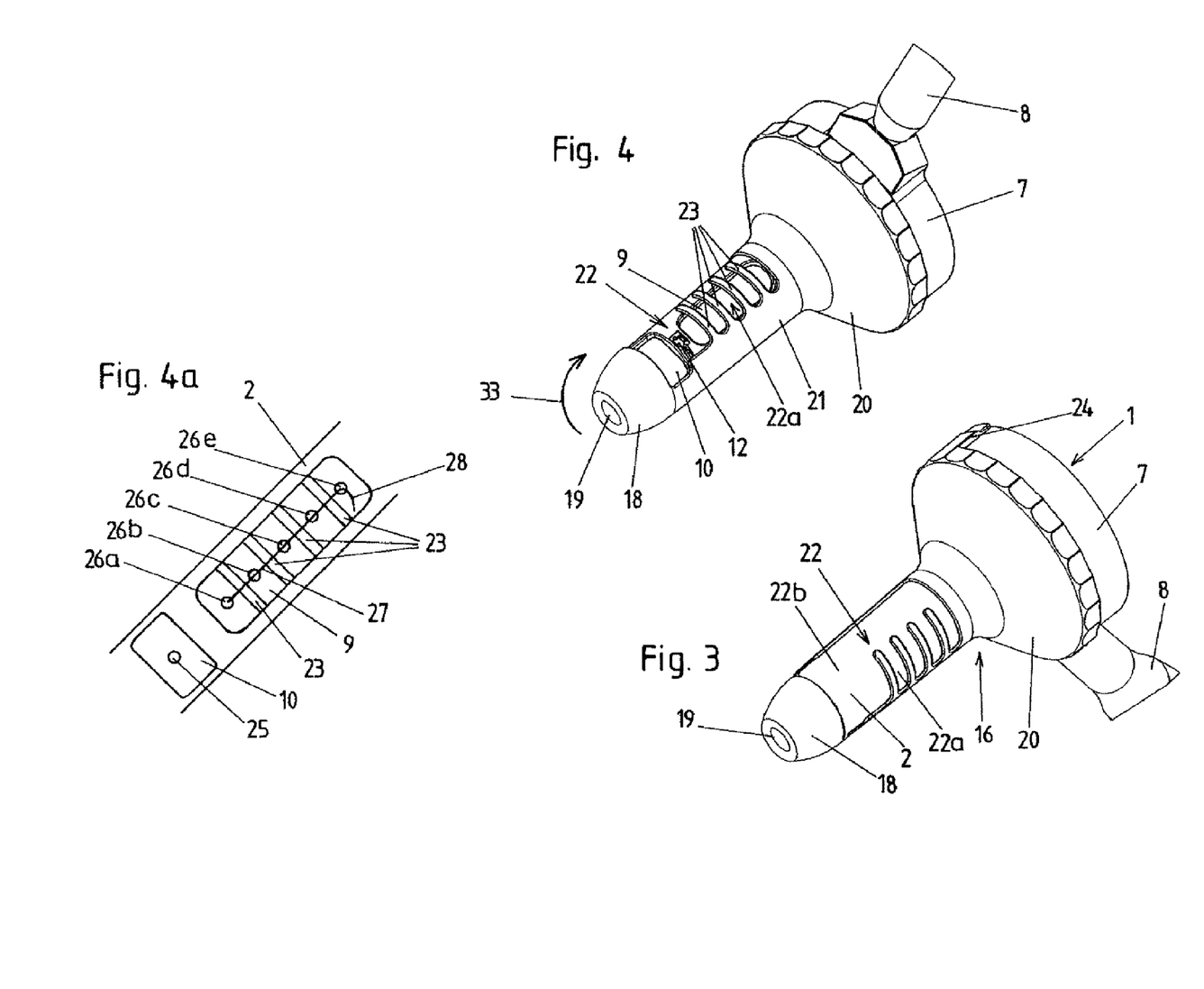
FIG. 3 shows the closed position of the device, which position is chosen upon insertion into the rectum of the patient.
FIG. 4 shows the open position in which a purse-string suture is applied to the mucosa.
FIG. 4a shows a view of the operation window from the inside.
Figure 5:
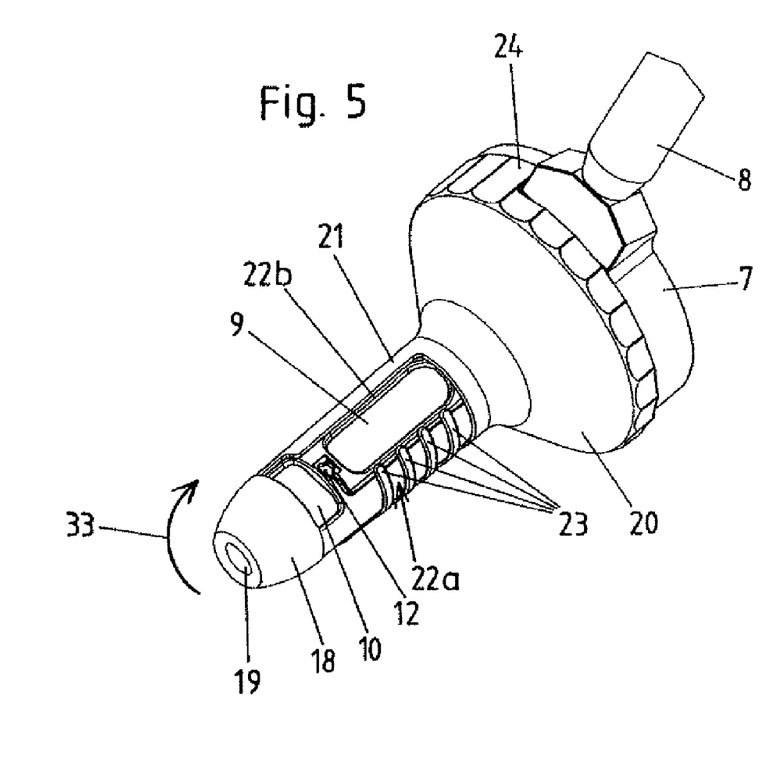
FIG. 5 shows the position of the closing device shortly before the purse-string suture is made ready.

FIG. 3 shows the closed position of the device, in which position it is inserted into the rectum of the patient at the start of the operation. In this position, the closing device 16 is turned relative to the tube 1 in such a way that the closed areas of the closure shell wall 21 completely cover the ligature opening 10 and also the tube shell opening 9. The closure shell opening 22 is correspondingly closed by the tube shell wall 2 lying on the inside. After insertion into the rectum, the open position shown in FIG. 4 is reached by turning the closing device 16 relative to the tube 1. By means of the abutment 24 of the closing device 16, and from corresponding markings on the holder 7 of the tube 1, it is possible to tell when this position has been reached. The ultrasound probe 12 can now be used to search for the artery that is to be operated on. When the latter has been found and, by way of the ligature opening 10 and tube shell opening 9, has been made accessible to the surgical instrument guided through the inner hollow space 5 of the tube 1, the stitches shown schematically in FIG. 4a can be applied. Here, 25 symbolizes the known HAL operation in the ligature opening 10. By contrast, the purse-string suture depicted by the stitches 26a to 26e is applied in the mucosa by way of the tube shell opening 9. For this purpose, the procedure starts with the distal stitch 26a. Thereafter, the stitches 26b, c, d and e are applied one after the other using the same continuous thread 27. The excess length 28 remains then at the proximal end of the thread 27. During this part of the operation, the mucosa is supported by the webs lying across the tube shell opening 9 in this position, such that the mucosa cannot be pressed too far through the tube shell opening 9 into the inner hollow space 5 of the tube 1. When an operating stage shown in FIG. 4a has been completed, the closing device can be turned further in the circumferential direction 33 until the abutment 24 of the closing device 16 abuts against the base of the handgrip 8. When this position shown in FIG. 5 is reached, the bars 23 are no longer arranged in front of the tube shell opening 9. The second portion 22b of the closure shell opening 22 is congruent with the tube shell opening 9. FIG. 5a shows the view corresponding to FIG. 4a looking from the interior of the hollow space 5 of the tube 1 to the mucosa and the HAL operation 25 and the purse-string suture formed by means of the thread 27. After the bars 23 are drawn back, the proximal end 28 of the thread 27 can be tied to the distal stitch 26a, the proximal stitch 26e being guided to the distal stitch 26a. Further HAL operations can be carried out and purse-string sutures applied on other arteries after turning the whole device within the rectum. It is often necessary to operate on three or more mucosal prolapses.

If, contrary to the example shown, the stitches 26a to 26e are applied not with a continuous thread 27 but with individual threads, it is also conceivable, as has already been indicated above, to design with webs 23 with such a length that they extend across the entire closure shell opening 22. The step of turning from the position shown in FIG. 4 to the position shown in FIG. 5 is then also omitted.

Figure 5A:
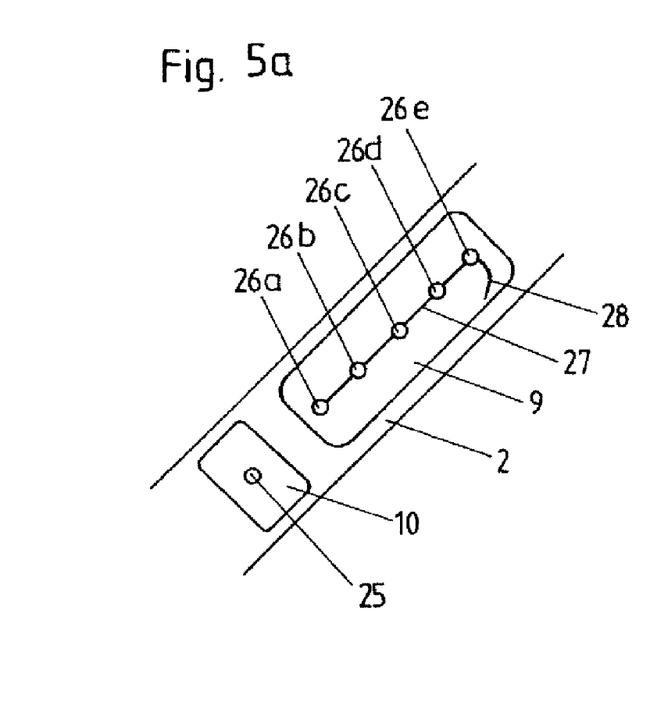
FIG. 5a shows a correspondingly schematic view of the mucosa from the direction of the inner hollow space of the tube.

The tube 1 of the device shown in the illustrative embodiment, however, can be used for more than a HAL operation or for applying a purse-string suture as shown in FIGS. 4a and 5a. It is also possible to treat a hemorrhoid prolapse by rubber band ligation. This kind of operation is known per se and is explained in EP 1 234 539 with reference to FIG. 12, such that it is not necessary to give details here of the surgical technique itself. It will be noted, however, that the use of the closing device 16 can be dispensed with in this operation. The tube 1 is inserted into the rectum of the patient directly, i.e. without the closing device 16. The operation can then be performed through the distal opening 15 of the tube shell wall 2. To make the insertion into the rectum as painless as possible and easy to do, provision is made, according to a particular aspect of the invention, for a push-in body 29 to be pushed into the inner hollow space 5 of the tube 1 prior to insertion of the device into the rectum. The distal end of the push-in body 29 expediently has a substantially conical shape and protrudes distally beyond the tube shell wall 2 in the pushed-in state.

Figures 6A, 6B, 7:
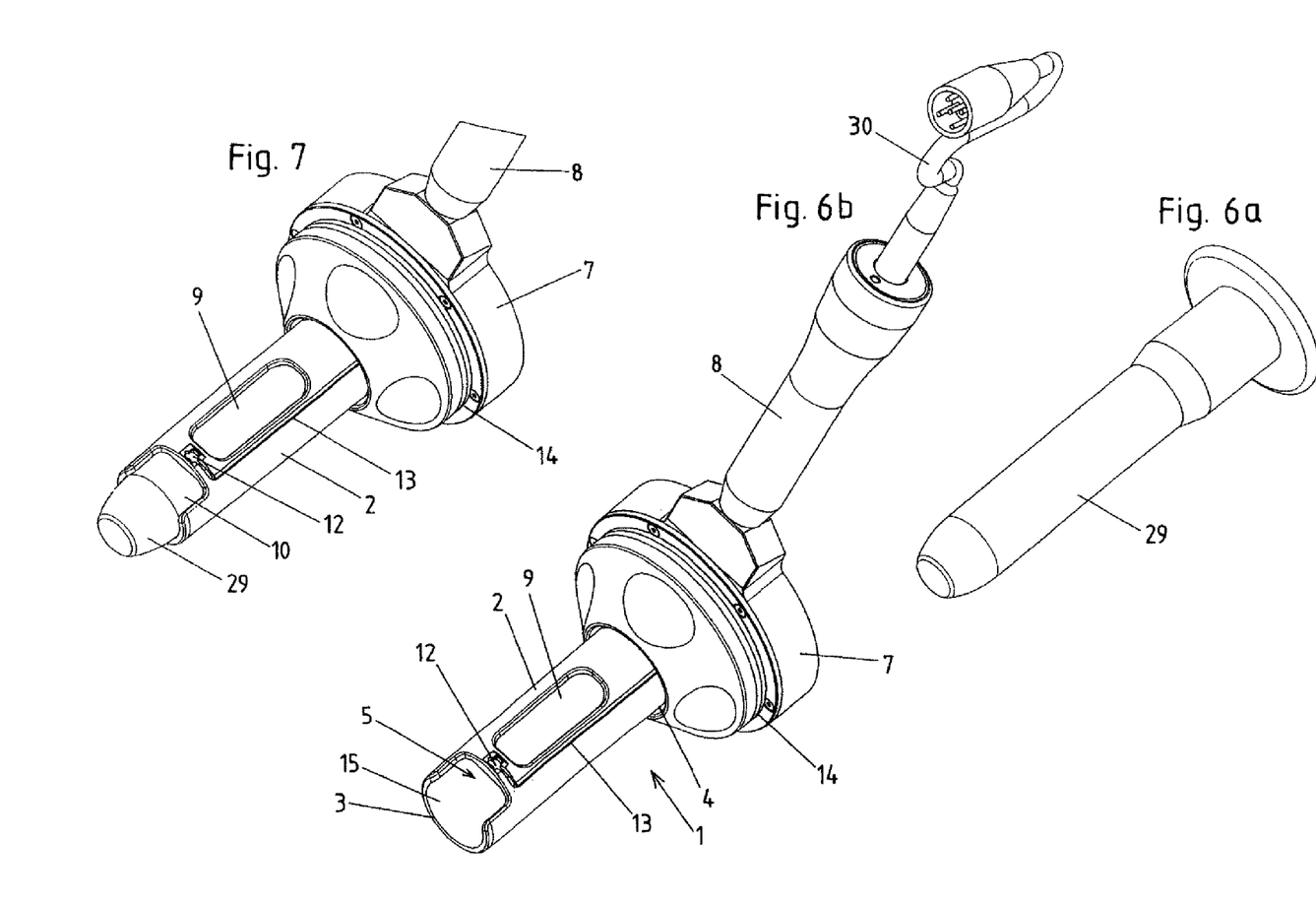

To perform the rubber band ligation, the push-in body is then removed before the instruments needed for the operation are inserted into the hollow space 5. FIGS. 6a to 7 show the tube 1 with push-in body 29. They also show the connecting cable 30 for the ultrasound sensor 12 and for any other surgical aids with which the device may be provided.

The dimensions of the device and of the openings in the tube shell wall 2 and closure shell wall 21 are expediently in the range known from the prior art. Thus, the axial length of the tube 1 protruding from the holder 7 is preferably 60 to 100 mm. The longitudinal extent of the tube shell opening 9 is expediently between 40 and 80 mm and its width is expediently between 8 and 20 mm.

Various modifications to the described illustrative embodiments are conceivable and possible without departing from the scope of the invention as defined in the claims.

KEY TO REFERENCE SIGNS 1 tube
2 tube shell wall
3 distal end of the tube shell wall
3' distal end of the tube shell opening
4 proximal end of the tube shell wall
4' proximal end of the tube shell opening
5 inner hollow space of the tube
6 longitudinal axis
7 holder
8 handgrip
9 tube shell opening
10 ligature opening
11 intermediate web
12 ultrasound sensor
13 channel
14 guide
15 distal opening of the tube shell wall
16 closing device
17 hollow space in the closure shell wall
18 distal portion of the closing device
19 distal opening of the closure shell wall
20 guide portion of the closing device
21 closure shell wall
22 closure shell opening
22a first portion
22b second portion
23 web
24 abutment
25 HAL operation
26a stitch of the purse-string suture
26b stitch of the purse-string suture
26c stitch of the purse-string suture
26d stitch of the purse-string suture
26e stitch of the purse-string suture
27 thread
28 proximal end of the thread
29 push-in body
30 connecting cable
31 distal end of the closure shell wall
31' distal end of the closure shell opening
32 proximal end of the closure shell wall
32' proximal end of the closure shell opening
33 circumferential direction

The invention claimed is:

1. A device for use in the treatment of a hemorrhoid prolapse, comprising:
   a tube with a tube shell wall and a closing device with a closure shell wall enclosing a hollow space,
   wherein the tube shell wall can be mounted displaceably or rotatably or displaceably and rotatably in the hollow space of the closure shell wall, and the tube shell wall and the closure shell wall can be inserted, individually or jointly, into a rectum of a patient,
   wherein the tube shell wall has at least one tube shell opening, and the closure shell wall has at least one closure shell opening, and the tube shell opening and the closure shell opening can be made to lie at least partially congruent with each other in at least one open position, wherein at least one bar is provided which is fixed to at least one shell wall selected from a group consisting of the tube shell wall and the closure shell wall and protrudes at least partially into at least one opening selected from a group consisting of the tube shell opening and the closure shell opening.

2. The device as claimed in claim 1, wherein several bars are arranged on at least one shell wall selected from the group consisting of the tube shell wall and the closure shell wall and protrude at least partially into at least one opening selected from the group consisting of the tube shell opening and the closure shell opening.

3. The device as claimed in claim 1, wherein at least one shell wall selected from the group consisting of the tube shell wall and the closure shell wall are/is elongate between a distal end and a proximal end.

4. The device as claimed in claim 1, wherein apart from openings provided therein, at least one shell wall selected from the group consisting of the tube shell wall and the closure shell wall are/is at least partially rotationally symmetrical with respect to a longitudinal axis.

5. The device as claimed in claim 1, wherein apart from openings provided therein, at least one shell wall selected from the group consisting of the tube shell wall and the closure shell wall are/is at least partially cylindrical or conical or frustoconical.

6. The device as claimed in claim 1, wherein at least one opening selected from the group consisting of the tube shell opening and the closure shell opening are/is elongate between their distal end and their proximal end.

7. The device as claimed in claim 1, wherein each bar is spaced apart from the distal end and from the proximal end of at least one opening selected from the group consisting of the tube shell opening and the closure shell opening.

8. The device as claimed in claim 1, wherein in the case of several bars, each two adjacent bars are spaced apart from each other and preferably extend parallel to each other.

9. The device as claimed in claim 8, wherein in the case of several bars, each two adjacent bars are spaced apart from each other and extend parallel to each other.

10. The device as claimed in claim 1, wherein each bar is elongate, and its longitudinal extent is substantially perpendicular to a longitudinal axis of at least one shell wall selected from the group consisting of the tube shell wall and the closure shell wall.

11. The device as claimed in claim 1, wherein each bar is curved in a circumferential direction like the tube shell wall or the closure shell wall.

12. The device as claimed in claim 1, wherein each bar is formed integrally on at least one shell wall selected from the group consisting of the tube shell wall and the closure shell wall.

13. The device as claimed in claim 1, wherein the bar or the bars extend across only a first portion of at least one opening selected from the group consisting of the tube shell opening and the closure shell opening, and a second portion of the at least one opening selected from the group consisting of the tube shell opening and the closure shell opening is free of bars.

14. The device as claimed in claim 13, wherein the second portion extends from the distal end to the proximal end of the at least one opening selected from the group consisting of the tube shell opening and the closure shell opening.

15. The device as claimed in claim 1, wherein each bar has one end free and one end arranged on at least one shell wall selected from the group consisting of the tube shell wall and the closure shell wall.

16. The device as claimed in claim 1, wherein at least one shell wall selected from the group consisting of the tube shell wall and the closure shell wall has a distal open end.

17. The device as claimed in claim 1, wherein the shape of the outer surface of the tube shell wall corresponds so exactly to the shape of the inner surface of the closure shell wall that, upon insertion of the tube shell wall into the hollow space of the closure shell wall, a snug fit can be obtained, except for the play required for insertion and turning.

18. The device as claimed in claim 1, wherein an ultrasound sensor for locating an artery is provided.

19. The device as claimed in claim 18, wherein the ultrasound sensor for locating an artery is provided on or in the tube shell wall.

20. The device as claimed in claim 1, wherein the tube shell wall comprises, in addition to the tube shell opening, a ligature opening separated from the latter by an intermediate bar.

21. The device as claimed in claim 1 wherein the tube shell wall comprises, in addition to the tube shell opening, a ligature opening separated from the latter by an intermediate bar, and wherein an ultrasound sensor is arranged on the intermediate bar.

22. The device as claimed in claim 21 wherein the ultrasound sensor is provided for locating an artery in the area of the ligature opening or of the tube shell opening.

23. The device as claimed in claim 1, wherein the tube shell wall encloses a hollow space which is open toward the proximal end for insertion of surgical instruments.

* * * * *

UNITED STATES PATENT AND TRADEMARK OFFICE
CERTIFICATE OF CORRECTION

PATENT NO.         : 8,394,012 B2
APPLICATION NO.    : 12/597400
DATED              : March 12, 2013
INVENTOR(S)        : Gerhard Szinicz Page 1 of 1

It is certified that error appears in the above-identified patent and that said Letters Patent is hereby corrected as shown below:

Title Page

Item (73): Please delete "(AU)" and replace it with -- (AT) --

Signed and Sealed this
Twelfth Day of November, 2013

Teresa Stanek Rea
*Deputy Director of the United States Patent and Trademark Office*